United States Patent [19]

Tapper et al.

[11] 4,340,047

[45] Jul. 20, 1982

[54] IONTOPHORETIC TREATMENT APPARATUS

[75] Inventors: Robert Tapper, 175 Acari Dr., Los Angeles, Calif. 90049; Gordon F. Sweeley, Grants Pass, Oreg.

[73] Assignee: Robert Tapper, Los Angeles, Calif.

[21] Appl. No.: 119,844

[22] Filed: Feb. 8, 1980

Related U.S. Application Data

[62] Division of Ser. No. 952,341, Oct. 18, 1978, Pat. No. 4,301,794.

[51] Int. Cl.³ .............................................. A61N 1/30
[52] U.S. Cl. ............................. 128/207.21; 128/419 R
[58] Field of Search ............ 128/207.21, 419 R, 419 S, 128/420 R, 421, 422, 423 R, 803

[56] References Cited

U.S. PATENT DOCUMENTS

| | | | |
|---|---|---|---|
| 2,263,205 | 11/1941 | Conrad | 128/207.21 |
| 3,215,139 | 11/1965 | Dietz | 128/207.21 |
| 3,289,671 | 12/1966 | Troutman | 128/207.21 X |
| 3,563,247 | 2/1971 | Bowers | 128/422 |
| 3,645,267 | 2/1972 | Hagfors | 128/421 |
| 3,955,583 | 5/1976 | Horauf | 128/420 R |
| 4,019,510 | 4/1977 | Ellis | 128/207.21 |
| 4,116,238 | 9/1978 | Pettijohn | 128/630 |
| 4,141,359 | 2/1979 | Jacobsen et al. | 128/207.21 |

FOREIGN PATENT DOCUMENTS 707011  3/1965  Canada ............................ 128/419 R Primary Examiner—Lee S. Cohen
Attorney, Agent, or Firm—Fulwider, Patton, Rieber, Lee & Utecht

[57] ABSTRACT

A method and apparatus for applying iontophoretic treatment to a living body is provided by which a unidirectional treatment current is periodically interrupted by a relatively short pulse of current in the opposite direction in order to prevent the formation of undesirable vesicles and bulla in the skin being treated. The apparatus and method are arranged to impose the treatment current gradually at the beginning of each treatment.

7 Claims, 2 Drawing Figures

IONTOPHORETIC TREATMENT APPARATUS

This is a division, of application Ser. No. 952,341, filed Oct. 18, 1978, now U.S. Pat. No. 4,301,794.

BACKGROUND OF THE INVENTION

This invention relates to apparatus for effecting an electrotherapeutic treatment on a living body, and more particularly, to the application of an iontophoretic treatment topically to the skin of a human body.

Direct current electrotherapeutic treatments have been employed in the past for their polar effects on ionized molecules, causing the ionized molecules to be driven through the skin, usually superficially. This phenomenon is known as iontophoresis, and it has been employed for the introduction of medicants, or even simply moisture, into the skin of a patient.

More specifically, some ions of zinc and copper can be employed in the treatment of some skin infections, and chlorine ions have been employed for the loosening of superficial scars. Further, vasodilating drugs can be used in rheumatic and peripheral vascular infections, and skin anesthesia can be produced by iontophoresis of local anesthetic drugs. It has been suggested that application of direct current to carefully selected areas of a living body can produce anesthetic effects (see Limoge, *An Introduction To Electroanesthesia*, 1975, University Park Press).

Further, F. Levitt in "Archives of Dermatology", Vol. 98 No. 5, November 1968, reports on pp. 505–507 the production of long term anhidrosis by iontophoretic treatment of the feet or hands. His test results indicate that the treatment inhibits perspiration where the electric current is applied.

Although the above-mentioned iontophoretic treatments have been found to be effective, they are also known to be accompanied by undesirable effects such as the occurrence of iontophoretic burns in the treated area as well as the formation of undesirable vesicles and bulla, and redness of the skin in the treated area. An apparatus and method for preventing these iontophoretic burns are disclosed in copending applications Ser. Nos. 806,393 filed June 13, 1977 and 940,777 filed Sept. 8, 1978, now U.S. Pat. Nos. 4,164,226 and 4,211,222, respectively. However, the apparatus and method disclosed in those applications have been found not to be adequately effective for preventing the formation of vesicles, bulla and redness of the skin in the treated area.

Accordingly, there has existed a need for a convenient and effective apparatus and method for preventing the formation of vesicles, bulla and redness of the skin in an area subjected to an iontophoretic treatment. As will become apparent from the following, the present invention satisfies that need.

SUMMARY OF THE INVENTION

The present invention resides in a means for applying electrical energy topically to the skin of a human body, and by which undesired side effects are greatly minimized and may be eliminated. Moreover, the device of the present invention is relatively inexpensive to manufacture, is trouble free and reliable in use, and is arranged to be safely operated for self-treatment by an average person in normal home use.

More specifically, the present invention provides apparatus for applying an iontophoretic treatment which includes conducting direct current through the skin of the body, and periodically reversing the current and conducting a relatively short pulse of current through the skin in the opposite direction. It has been discovered that by intermittently including relatively short pulses of current in a direction opposite the direction of the normal direct current treatment, the undesirable formation of vesicles, bulla and reddening of the skin in the treated area is greatly reduced or even eliminated.

Electronic circuitry is provided to automatically impose the reverse pulse of current at regular intervals of time, and the device can be adjusted to conduct the iontophoretic treatment at any desired direct current level. According to a further feature of the invention, the apparatus and method are arranged to impose the treatment current gradually at the beginning of each treatment period so that the invention can be safely employed for self-treatment by an average person in the home.

Other features and advantages of the present invention will become apparent from the following detailed description, taken in conjunction with the accompanying drawings, which illustrate, by way of example, the principles of the invention.

DETAILED DESCRIPTION

As shown in the exemplary drawings, the present invention is embodied in apparatus for applying iontophoretic treatment to a living body. In this treatment, direct current is applied topically to the skin by a pair of electrodes 10, illustrated diagrammatically in FIG. 2.

In order to accomplish the desired results, the iontophoretic treatment generally consists of a constant flow of unidirectional current between the electrodes. Depending upon the kind of iontophoretic treatment being applied, this current can be applied to the body at a rate of between a small fraction of a milliampere (ma) and about fifty ma. In an iontophoretic treatment for the production of anhidrosis, for example, a treatment current of between about four and fifteen ma is preferred.

Figure 1:
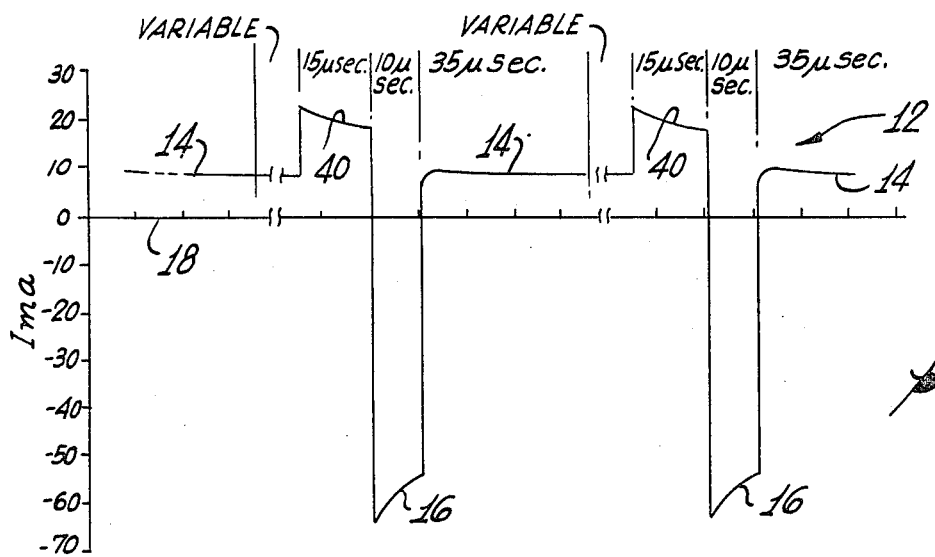
FIG. 1 is a graph showing a current waveform which can be used in the present invention.

A current versus time waveform, indicated generally by reference numeral 12 in FIG. 1, is illustrated as having a treatment portion 14 which, in this instance, is a relatively long steady current of about eight ma. in the positive or forward direction. Heretofore, iontophoretic treatments have been effected by application of a pure direct current to a user.

In accordance with the present invention, the iontophoretic treatment portion 14 of the waveform 12 is periodically interrupted by a relatively short pulse 16 of current in the opposite direction in order to prevent the formation of undesirable vesicles, bulla or redness of the user's skin in the treated area. It should be understood that the reference to a short reverse pulse 16 is not to be construed as referring to a conventional alternating current waveform. Rather, the waveform 12 represents a substantially direct current treatment interrupted at regular intervals of time by the reverse pulse 16, thereby forming the asymmetrical waveform 12.

As will be described in greater detail hereinafter, the apparatus of the present invention is further arranged to impose the treatment current gradually at the beginning of each treatment period. By this arrangement, inadvertent electric shocks to the user are prevented so that the invention can be safely employed for self-treatment in the home by an average person of ordinary intelligence. Further, the apparatus of the present invention is relatively inexpensive to manufacture, and is trouble free and reliable in use.

It has been discovered that the undesirable formation of vesicles, bulla and redness of the skin in an area subjected to an iontophoretic treatment can be greatly reduced or even eliminated by periodic inclusion of the reverse pulse 16 into the waveform 12. More specifically, it has been found that these undesirable phenomena are completely eliminated when the waveform 12 is adjusted so that the energy indicated by the waveform above the zero current reference line 18 is substantially equal to the energy indicated by the waveform below the reference line 18.

The portions of the waveform 12 above and below the reference line 18 indicate the amount of energy applied in the forward direction and the reverse direction, respectively.

Unfortunately, when the reverse energy is arranged to be substantially equal to the forward energy, thereby eliminating the above-mentioned undesirable effects, it has been found that the desirable iontophoretic treatment is also eliminated. As a corollary to this discovery, it has been determined that whenever the waveform 12 is adjusted so that the forward energy exceeds the reverse energy, some desirable treatment occurs.

With the forward energy only slightly greater than the reverse energy, the undesirable vesicles and redness of the skin are eliminated, but the period required to achieve the desired results of the iontophoretic treatment becomes so long that the apparatus would not be considered practical by many. Accordingly, it has been found that a satisfactory compromise is achieved between forward energy for treatment and reverse energy for prevention of undesirable effects when the ratio of forward energy to reverse energy is between about 2:1 and 7:1.

More specifically, when operating at a treatment current of about fourteen ma, a ratio of forward energy to reverse energy of about 2.3:1 has been found to achieve the desired results. Naturally, other ratios can be employed in practicing this invention, but ratios within the above-mentioned range have been found to be satisfactory in reducing or preventing vesicle formation and reddening of the user's skin.

Figure 2:
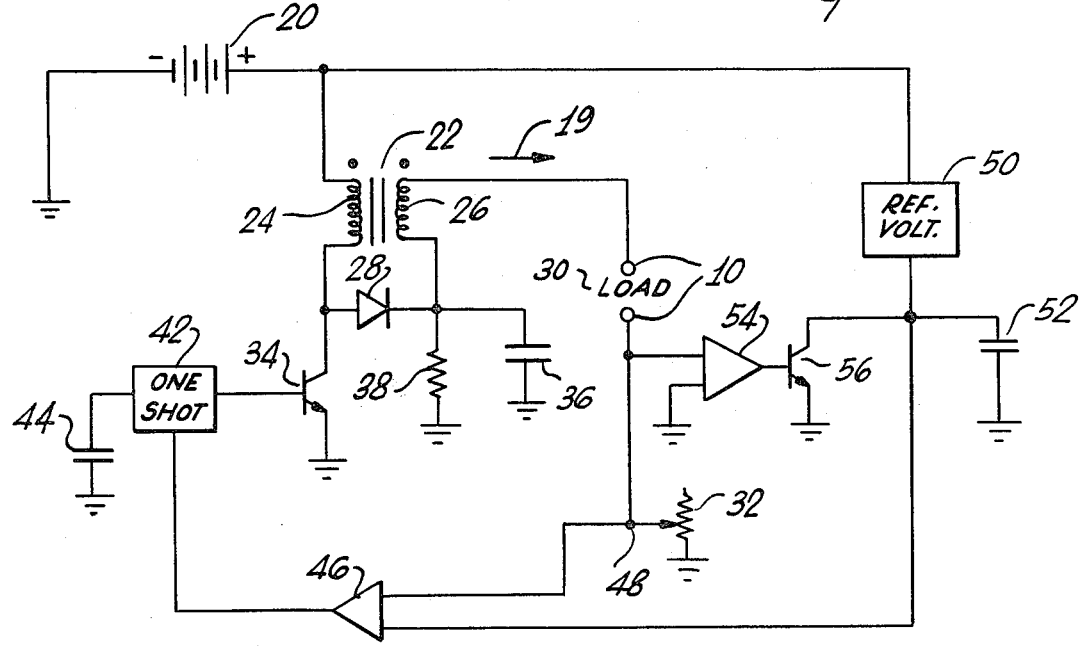
FIG. 2 is a schematic diagram of a preferred apparatus for accomplishing the method of the present invention.

In order to impose the waveform 12 on the electrodes 10, electronic circuitry is provided, as illustrated in the schematic diagram of FIG. 2. It will be appreciated that various electronic means can be provided to interrupt a steady unidirectional flow of current with a relatively short reverse pulse of current at regular intervals of time. The circuit represented by the diagram of FIG. 2 is an example of such an electronic means, and is the presently preferred embodiment of this invention.

For providing a steady flow of unidirectional current across the electrodes 10, in a forward direction indicated diagrammatically by an arrow 19, a source of direct current, herein illustrated as a battery 20, is connected to a transformer 22 having a primary winding 24 and a secondary winding 26. The battery is connected to one terminal of the primary winding 24, and a diode 28 is coupled between the other terminal of the primary winding and one terminal of the secondary winding with the anode connected to the primary terminal and the cathode connected to the secondary terminal. A storage capacitor 36, and a resistor 38 are coupled in parallel between the cathode of the diode and ground, whereby a direct current path is formed from the battery 20 to the capacitor 36, via the primary winding 24 and the diode 28.

When a load 30 is imposed across the electrodes 10, a steady flow of direct current is permitted to flow from the battery 20 through the primary winding 24, the diode 28, the secondary winding 26, the load 30, and to ground through a variable resistor 32. The variable resistor 32 is used to control the amount of current which is permitted to flow across the load 30.

The apparatus includes switch means for imposing a succession of reverse current pulses 16 on the load 30. The switch means includes the transformer 22, the diode 28, and a shunt transistor 34, the shunt transistor being connected to the end of the primary winding 24 opposite the battery 20. When the transistor 34 is turned on for a short period of time, a surge of current will flow through the primary winding 24 inducing a similar increase in current through the secondary winding 26 and across the load 30, discharging the capacitor 36. Upon abruptly turning the transistor 34 off, the magnetic flux generated by the surge of current through the transformer 22 will collapse, causing a temporary reversal of current through the secondary winding 26, to charge the capacitor 36.

As illustrated in the exemplary waveform 12 in FIG. 1, when the shunt transistor 34 is turned on for 15 microseconds, a period of increased current 40 appears in the waveform 12. This increased flow continues while the shunt transistor 34 is on, and decays slightly due to a gradual decrease in the rate of change of current in the primary winding 24 of the transformer 22 and to a gradual discharging of the capacitor 36.

The above-mentioned reverse flow of current through the secondary winding 26 appears in the waveform 12 as the reverse pulse 16. The amplitude of this reverse pulse is also shown as decaying because of a gradual decrease in the rate of change of current in the primary winding 24 as the magnetic flux in the transformer collapses, and because the load 30, which is ordinarily human skin, is known to have some capacitance. An electronic model of human skin showing this capacitance can be found in an article by Erich A. Pfeiffer entitled: "Electrical Stimulation of Sensory Nerves With Skin Electrodes For Research, Diagnosis, Communication and Behavorial Conditioning: A Survey", Medical and Biological Engineering; Vol. 6, pp 637–651; 1968.

The shunt transistor 34 is turned on by a one-shot 42 which is arranged to turn the transistor on for a short period of time, and as mentioned above, in this example the transistor is turned on for 15 microseconds and then abruptly turned off. The one-shot 42 is further arranged, by connection with an external timing capacitor 44, to wait for an additional period of time after the transistor 34 has been turned off before the one-shot can again be triggered to turn the transistor on. The value of the timing capacitor 44 can be chosen to impose any desired waiting period on the one-shot 42, and in the example illustrated in FIG. 1, a 45 microsecond waiting period is shown. This waiting period consists of the reverse pulse 16, having a width of about 10 microseconds, and a minimum iontophoretic treatment period of 35 microseconds.

The one-shot 42 is triggered by frequency adjusting means that includes a control comparator 46 and the variable resistor 32. The control comparator compares the voltage at a terminal 48 on the variable resistor 32 to a prescribed internal reference voltage maintained by a voltage reference device 50. The comparator 46 triggers the one-shot 42 whenever the voltage at the terminal 48 drops below the voltage supplied by the reference 50.

By this arrangement, when the device is being operated at a relatively high treatment current 14, the voltage at the terminal 48 will drop below the reference voltage before the waiting period has elapsed, and therefore, the one-shot will always be triggered immediately after the waiting period. Conversely, when the device is operated at a relatively low treatment current 14, the above-mentioned inherent capacitance in the load 30 will cause the voltage at the terminal 48 to drop more slowly, and the comparator 46 will trigger the one-shot at some time after the waiting period has elapsed.

Accordingly, it will be appreciated that the period of time between triggering the one-shot 42 to turn on the transistor 34 will vary according to the level of treatment current chosen by the user and the actual capacitance of the skin represented by the load 30. This variable period of time is illustrated in the waveform 12 by a broken time scale and the legend "variable".

Further, it will be appreciated that this arrangement provides for relatively frequent occurrences of reverse pulses 16 when a high treatment current 14 is employed, and relatively infrequent occurrence of reverse pulses 16 when a lower treatment current 14 is employed. This variance in frequency of reverse pulses 16 results in a varying ratio of forward energy to reverse energy at different treatment currents 14, but the value of the timing capacitor 44 is chosen to maintain this ratio within a range that has been found to be satisfactory, as described above.

Another important feature of the present invention is its facility to be safely employed in the home by an average person of ordinary intelligence. This feature is desirable because, if the treatment current 14 is imposed on the user too rapidly, the user may experience discomfort in the form of an electric shock. Accordingly, the present apparatus of the invention includes delay means arranged to impose the treatment current gradually whenever a load 30 is placed across the electrodes 10 and the device is activated. Further, if the load is removed from the electrodes during operation of the device and subsequently reimposed thereon, the delay means of the apparatus is arranged to gradually increase the current until the treatment current 14 is again achieved.

Toward the foregoing ends, when the device is originally activated with a load 30 across the electrodes 10, the voltage reference device 50, which is connected to the battery 20, slowly charges a delay capacitor 52 up to the reference voltage. Consequently, the current flowing from the battery 20 through the load 30 will rise slowly as the capacitor 52 charges. Preferably, the value of the delay capacitor 52 is chosen so that the current through the load 30 will rise to the treatment level in about two seconds. When the delay capacitor has fully charged, the prescribed reference voltage will be applied to the control comparator 46, and normal operation of the present invention can proceed as described above.

If the load 30 is removed during operation of the apparatus thereby creating an open circuit between the electrodes 10, a window comparator 54 will detect the open circuit and rapidly discharge the delay capacitor 52 through a transistor 56. The discharge of the delay capacitor 52 will bring the reference voltage on the control comparator 46 to zero and inhibit the one-shot 42 from being triggered. When the load is reimposed across the electrodes 10, the delay capacitor 52 will once again be charged gradually to the prescribed reference voltage, thereby causing the current across the load to gradually rise correspondingly.

From the foregoing, it will be appreciated that the present invention provides an effective apparatus for applying an iontophoretic treatment to the skin of a living body while greatly reducing or preventing the formation of undesirable vesicles, bulla or redness of the skin in the treated area. Further, the present invention is arranged to be safely employed for self-treatment by a person of ordinary intelligence, and the apparatus of this invention can be manufactured conveniently and economically, and is trouble free and reliable in use.

While a particular form of the invention has been illustrated and described, it will be apparent that various modifications can be made without departing from the spirit and scope of the invention.

I claim:

1. An apparatus for applying an iontophoretic treatment to a living body, comprising:
    a pair of electrodes adapted to contact the skin of the body, in spaced relationship to each other;
    a supply capacitor coupled across the electrodes for supplying electrical current for conduction through the body, from one electrode to the other;
    switch means for charging the supply capacitor at regular intervals of time; and
    means for controllably adjusting the frequency at which the switch means operates to charge the supply capacitor, to adjust the magnitudes of the voltage on the capacitor and the electrical current supplied by the capacitor, correspondingly.

2. An apparatus as defined in claim 1, wherein the means for controllably adjusting includes delay means, operable when the iontophoretic treatment is initiated by the apparatus, for slowly increasing the frequency at which the switch means operates, whereby application of full treatment current is delayed for a prescribed time duration.

3. An apparatus as defined in claim 2, wherein:
    the delay means includes
        a delay capacitor, and
        means for charging the delay capacitor to a prescribed reference voltage; and
    the frequency at which the switch means operates to charge the supply capacitor varies in accordance with the charge on the delay capacitor.

4. An apparatus as defined in claim 1, wherein the switch means charges the supply capacitor by a substantially constant amount each time it operates.

5. An apparatus for applying an iontophoretic treatment to a living body, while minimizing concomitant vesicle formation, the apparatus comprising:
    first and second electrodes adapted to contact the skin of the body, in spaced relationship to each other;
    direct current means electrically coupled to the two electrodes for conducting direct current through the body, from the first electrode to the second electrode; and reverse pulse means electrically coupled to the two electrodes for conducting a short duration pulse of current through the body, from the second electrode to the first electrode, at regular intervals of time, the reverse pulse means including a transformer having a primary winding and a secondary winding, the secondary winding being electrically coupled to the two electrodes, and means electrically coupled to the primary winding of the transformer for conducting a primary current pulse of prescribed magnitude and duration through the primary winding, at regular intervals of time, termination of each primary current pulse inducing in the secondary winding the short duration pulse of current for conduction through the body.

6. An apparatus for applying an iontophoretic treatment to a living body, while minimizing concomitant vesicle formation, the apparatus comprising:

first and second electrodes adapted to contact the skin of the body, in spaced relationship to each other;

direct current means electrically coupled to the two electrodes for conducting direct current through the body, from the first electrode to the second electrode;

reverse pulse means electrically coupled to the two electrodes for conducting a short duration pulse of current through the body, from the second electrode to the first electrode, at regular intervals of time; and delay means for delaying the conduction of a full treatment current through the body, the delay means including a delay capacitor electrically coupled to the direct current means, the current conducted by the direct current means varying in accordance with the voltage on the delay capacitor, means for charging the delay capacitor in a prescribed fashion, whereby the direct current means conducts a full treatment current through the body only after a prescribed time duration, means for detecting an open circuit between the two electrodes and for generating a corresponding control signal, and means responsive to the control signal for rapidly discharging the delay capacitor.

7. In an apparatus for applying an iontophoretic treatment to a living body, the apparatus including a pair of electrodes adapted to contact the skin of the body, in spaced relationship to each other, and current means for conducting a treatment current through the body, from one electrode to the other, in a prescribed fashion, an improvement comprising:

delay means for delaying the conduction of a full treatment current through the body, the delay means including a delay capacitor electrically coupled to the current means, the current conducted by the current means varying in accordance with the voltage on the delay capacitor, means for charging the delay capacitor in a prescribed fashion, whereby the current means conducts a full treatment current through the body only after a prescribed time duration, means for detecting an open circuit between the two electrodes and for generating a corresponding control signal, and means responsive to the control signal for rapidly discharging the delay capacitor.

* * * * *